United States Patent

Nakazawa et al.

(10) Patent No.: US 9,440,904 B2
(45) Date of Patent: Sep. 13, 2016

(54) METHOD FOR PRODUCING UNSATURATED ALDEHYDE AND/OR UNSATURATED CARBOXYLIC ACID

(71) Applicant: Nippon Kayaku Kabushiki Kaisha, Tokyo (JP)

(72) Inventors: Yuuta Nakazawa, Yamaguchi (JP); Tatsuhiko Kurakami, Yamaguchi (JP); Kazuo Shiraishi, Gunma (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/903,418

(22) PCT Filed: Jul. 17, 2014

(86) PCT No.: PCT/JP2014/068994

§ 371 (c)(1),
(2) Date: Jan. 7, 2016

(87) PCT Pub. No.: WO2015/008815

PCT Pub. Date: Jan. 22, 2015

(65) Prior Publication Data

US 2016/0145181 A1 May 26, 2016

(30) Foreign Application Priority Data

Jul. 18, 2013 (JP) ................................. 2013-149136

(51) Int. Cl.
| | |
|---|---|
| *C07C 45/00* | (2006.01) |
| *C07C 51/00* | (2006.01) |
| *C07C 51/25* | (2006.01) |
| *C07C 45/35* | (2006.01) |
| *B01J 35/00* | (2006.01) |
| *B01J 23/00* | (2006.01) |
| *B01J 23/887* | (2006.01) |
| *B01J 35/02* | (2006.01) |
| *B01J 35/08* | (2006.01) |
| *B01J 37/00* | (2006.01) |

(52) U.S. Cl.
CPC ............ *C07C 51/252* (2013.01); *B01J 23/002* (2013.01); *B01J 23/8876* (2013.01); *B01J 35/0006* (2013.01); *B01J 35/023* (2013.01); *B01J 35/08* (2013.01); *B01J 37/0018* (2013.01); *B01J 37/0045* (2013.01); *B01J 37/0063* (2013.01); *C07C 45/35* (2013.01); *B01J 2523/00* (2013.01)

(58) Field of Classification Search
CPC ....... C07C 45/27; C07C 45/35; C07C 51/16; C07C 51/252; B01J 37/00; B01J 23/00
USPC .......................................... 568/449; 562/542
See application file for complete search history.

(56) References Cited

U.S. PATENT DOCUMENTS

| | | | |
|---|---|---|---|
| 4,837,360 | A | 6/1989 | Kadowaki et al. |
| 5,276,178 | A | 1/1994 | Onodera et al. |
| 6,632,965 | B1 | 10/2003 | Tanimoto et al. |
| 6,781,013 | B2 | 8/2004 | Tanimoto |

FOREIGN PATENT DOCUMENTS

| | | | | |
|---|---|---|---|---|
| EP | 1074538 A2 | * | 2/2001 | ............ B01J 23/002 |
| JP | 55-113730 A | | 9/1980 | |
| JP | 3-215441 A | | 9/1991 | |
| JP | 6-192144 A | | 7/1994 | |
| JP | 9-202741 A | | 8/1997 | |
| JP | 2001-48817 A | | 2/2001 | |
| JP | 2001-226302 A | | 8/2001 | |
| JP | 2007-511565 A | | 5/2007 | |

OTHER PUBLICATIONS

International Search Report and Written Opinion mailed Oct. 7, 2014 in corresponding PCT application No. PCT/JP2014/068994.

* cited by examiner

*Primary Examiner* — Sikarl Witherspoon
(74) *Attorney, Agent, or Firm* — Nields, Lemack & Frame, LLC

(57) ABSTRACT

Provided is a method capable of producing acrolein and/or acrylic acid, or methacrolein and/or methacrylic acid, stably in a high yield over a long period of time advantageously even in a high-load reaction, and the method is a method in which when preparing two or more kinds of catalysts having different formulations and stacking two or more layers in the axial direction of the tube, the catalysts are filled in such a manner that not only the component amount of bismuth relative to molybdenum decreases from the gas inlet side toward the gas outlet side, but also the component amount of iron relative to molybdenum increases from the gas inlet side toward the gas outlet side.

9 Claims, No Drawings

METHOD FOR PRODUCING UNSATURATED ALDEHYDE AND/OR UNSATURATED CARBOXYLIC ACID

TECHNICAL FIELD

The present invention relates to a method of subjecting an alkene to gas-phase catalytic partial oxidation with molecular oxygen or a molecular oxygen-containing gas in the presence of the complex metal oxide catalyst, thereby producing a corresponding unsaturated aldehyde and/or unsaturated carboxylic acid.

BACKGROUND ART

In the case of subjecting propylene to gas-phase catalytic partial oxidation with molecular oxygen, thereby producing acrolein and acrylic acid on an industrial scale, various problems are caused. As one of them, it is known that as the temperature to which a complex metal oxide catalyst (hereinafter referred to as "catalyst") is exposed increase, the deterioration of the catalyst is accelerated. In addition, it is also widely known that when an excessive oxidation reaction is promoted, the yield of a target product is lowered. Then, in order to increase the productivity of a target product under high-load circumstances where a raw material concentration or a space velocity is high, though it is necessary to increase the reaction bath temperature, thereby keeping a reaction rate of the catalyst at a high level, there is involved such a problem that when the reaction bath temperature is high as described above, a catalyst life becomes short. Furthermore, since the gas-phase catalytic partial oxidation of propylene or the like is an exothermic reaction, a local high-temperature portion (hot spot) is generated in a catalyst layer, so that the deterioration of the catalyst and the lowering of the yield become conspicuous. As for these problems, there have been made various proposals in the conventional techniques. For example, Patent Document 1 describes a method in which plural kinds of catalysts differing in occupying volume and calcination temperature, and/or kind and/or amount of alkali metal element from each other, are prepared and filled in a multitubular oxidation reactor in such a manner that the activity increases from the raw material gas inlet toward the outlet in the axial direction of the tube, thereby suppressing a hot spot temperature. This method is aimed to suppress excessive heat generation by filling the catalysts with controlled activity in the inlet side into which the high-concentration raw material gas is introduced. But, in regulating the activity by the occupying volume, there may be the case where a sufficient effect is not obtained because the size of the occupying volume of the catalyst is restricted by a reaction tube diameter; or there may be a possibility that in view of the matter that the catalysts are not uniformly filled, a designed reaction field is not realized, so that a sufficient catalytic performance is not exhibited. In addition, Patent Document 2 describes a method in which a supporting amount of the catalyst is increased from the raw material gas inlet side toward the outlet side to impose a ranking in the catalytic activity, thereby suppressing a hot spot temperature on the raw material gas inlet side, whereas on the outlet side where a highly active catalyst is filled, a gas-phase catalytic partial oxidation reaction is made to reach a conversion of the raw material required from the process standpoint. However, there is involved such a problem that in the catalyst on the raw material gas inlet side where the supporting amount is low, the life is short, whereas in the catalyst on the raw material gas outlet side, the amount of the active component is large, so that the layer of the catalytically active component becomes thick, whereby the reaction heat is accumulated within the catalyst, and the selectivity is lowered. In addition, Patent Document 3 describes a method in which by using annular catalysts, the hot spot temperature is suppressed, thereby making it possible to cope with the reaction under high-load circumstances. But, the annular catalysis also encounter such serious problems that when filled in a multitubular oxidation reactor, it is difficult to uniformly fill the catalysts from the standpoint of properties of the shape; and that from the standpoint of properties of a shaping method, the catalysts collapse or cause powdering because of low mechanical strength, so that not only the reaction tube is plugged, but also the catalytically active component falls down, whereby the catalytic performance is not sufficiently exhibited. Furthermore, Patent Document 4 discloses a technique in which by filling catalysts having a different ratio of bismuth and iron in each reaction tube having two or more reaction zones disposed therein along the axis of the tube in such a manner a total amount of bismuth and iron decreases from the ran material gas inlet toward the outlet, the sublimation of the molybdenum component is suppressed, thereby producing acrolein and acrylic acid stably in high yields over along period of time.

BACKGROUND ART DOCUMENT

Patent Document

Patent Document 1: JP-A-2001-226302
Patent Document 2: JP-A-H6-192144
Patent Document 3: JP-T-2007-511565
Patent Document 4: JP-A-2001-048817

SUMMARY OF INVENTION

Problem that Invention is to Solve

While the method of subjecting an alkene to a gas-phase catalytic partial oxidation reaction, thereby producing a corresponding unsaturated aldehyde and/or unsaturated carboxylic acid has already been partly industrialized, a more improvement in the catalytic performance and an innovative use method thereof ore demanded. On the occasion of contemplating to produce, from an alkene, a corresponding unsaturated aldehyde and/or carboxylic acid by using a multitubular oxidation reactor, a supply load of the alkene relative to the unit catalyst volume becomes high (also expressed as "high-load reaction"), so that it becomes necessary to increase the reaction bath temperature. As a result, the temperature within the catalyst layer is increased to bring about a lowering in catalytic activity and/or selectivity with time, whereby the yield of a target product is lowered. Thus, such is of a problem from the viewpoint of long-term use. The improvement in the catalytic activity makes it possible to achieve a decrease of the reaction bath temperature, a reduction of the running costs, and a prolongation of the catalyst life, and the improvement in the yield of a target product makes it possible to achieve a significant reduction of the production costs. In addition, in the case where even if a shaping method of the catalyst which is used for this gas-phase catalytic partial oxidation reaction is any method of tablet shaping, extrusion shaping, coating shaping, or others, the mechanical strength is low in the end, at the time of filling the catalyst in the multitubular oxidation reactor, the inside of the multitubular oxidation reactor is plugged due to powdering of the catalyst and exfoliation of the catalytically active component, resulting in bringing about an abnormal increase of pressure. Namely, in order to exhibit the original excellent activity and selectivity of the catalyst, a catalyst with high mechanical strength is needed. Furthermore, in order to decrease the reaction bath temperature, a catalyst with high activity is needed. However, in the conventional techniques, a significant lowering of the selectivity is followed due to high activation of the catalyst, and hence, a technique for producing highly active catalysts while keeping high selectivity and effectively combining them to produce a target product is problematic. Especially, as for highly active catalysts, unless they are used after thoroughly investigating a use method thereof, the hot spot temperature becomes excessively high, thereby causing a lowering of the yield. Furthermore, a runaway reaction would be possibly caused. In consequence, an object of the present invention is to provide a technique of making it possible to advantageously produce acrolein and/or acrylic acid, or methacrolein and/or methacrylic acid, even in a reaction under high-load circumstances, while making it possible to make the reaction bath temperature low.

Means for Solving Problem

In order to solve the foregoing problem, the present inventors made extensive and intensive investigations. As a result in a method of subjecting an alkene to gas-phase catalytic partial oxidation with molecular oxygen by using a multitubular oxidation reactor having a complex metal oxide catalyst filled therein, thereby producing a corresponding unsaturated aldehyde and/or unsaturated carboxylic acid, the present inventors paid attention to the amounts of bismuth and iron that are important among constitutional elements of the catalyst and made extensive and intensive investigations. As a result, they have found a technique in which when preparing two or more kinds of catalysts having different formulations and stacking two or more layers in the axial direction of the tube, thereby achieving multilayer filling, by filling the catalysts in such a manner that not only the component amount of bismuth relative to molybdenum decreases from the gas inlet side toward the gas outlet side, but also the component amount of iron relative to molybdenum increases from the gas inlet side toward the gas outlet side, a catalytic performance of the highly active catalyst is effectively exhibited, and the catalyst on the raw material gas inlet side becomes high in selectivity and long in life, whereas the catalyst on the raw material gas outlet side becomes conspicuously high in activity, whereby even in a high-load reaction, the reaction bath temperature can be controlled at a low level, and a target product is stably obtained in a high yields, leading to accomplishment of this invention. It is to be noted that Patent Document 4 describes she method of successively filling catalysts in which a total amount of bismuth and iron is decreased from the gas inlet toward the outlet of the catalyst layer for the purpose of suppressing scattering of the molybdenum component and describes the working examples in which the component amount of iron is made equal or decreased with a decrease of the component amount of bismuth. As a means of solving the problem held in the present invention, it is necessary to not only decrease the component amount of bismuth relative to molybdenum from the gas inlet toward the outlet but also increase the component amount of iron relative to molybdenum.

Specifically, the present invention is concerned with the following, (1) A method for producing an unsaturated aldehyde and/or an unsaturated carboxylic acid, the method comprising:
subjecting an alkene to gas-phase catalytic partial oxidation with molecular oxygen by using a multitubular oxidation reactor having a complex metal oxide catalyst filled therein, thereby producing a corresponding unsaturated aldehyde and/or unsaturated carboxylic acid,
wherein when preparing two or more kinds of catalysis having different formulations and stacking two or more layers in an axial direction of a tube, thereby achieving multilayer filling, the catalysts are filled in such a manner that not only a component amount of bismuth relative to molybdenum decreases from a gas inlet side toward a gas outlet side, but also a component amount of iron relative to molybdenum increases from the gas inlet side toward the gas outlet side.
(2) The production method as described in (1) above,
wherein the catalyst for producing an unsaturated aldehyde and/or an unsaturated carboxylic acid contains a compound represented by the following formula (1), the catalyst being prepared by a method in which in a step of preparing the compound represented by the following formula (1): a molybdenum component raw material is constituted of only an ammonium molybdate, and a weight of water for dissolution is 8.5 times or less relative to a weight of molybdenum contained in the ammonium molybdate; a bismuth component raw material is constituted of only bismuth nitrate, a weight of a nitric acid aqueous solution for dissolution is 2.3 times or more relative to a weight of bismuth contained in the bismuth nitrate, and a concentration of nitric acid of the nitric acid aqueous solution for dissolving bismuth nitrate therein is 10% by weight or more, and is filled in at least one layer on the most gas outlet side in the tube axis:

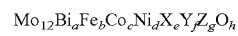

$$Mo_{12}Bi_aFe_bCo_cNi_dX_eY_fZ_gO_h \qquad \text{Formula (1)}$$

(wherein X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0; b=1 to 2.5; c=3 to 7; d=2 to 3.5; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 35 or less.)
(3) The production method as described in (1) or (2) above,
wherein a form of the complex metal oxide catalyst is a spherical coating catalyst in which catalytic active components are supported on a surface of an inert carrier
(4) The production method as described in any one of (1) to (3) above,
wherein a load of the alkene in the raw material gas to be supplied into the multitubular oxidation reactor is 120 times or more (converted in a standard state) relative to a unit catalyst volume per one hour.
(5) The production method as described in any one of (1) to (4) above.
wherein a load of the alkene in raw material gas to be supplied into the multitubular oxidation reactor is 140 times or more (converted in a standard state) relative to a unit catalyst volume per one hour.

(6) The production method as described in any one of (1) to (5) above,
wherein a load of the alkene in raw material gas to be supplied into the multitubular oxidation reactor is 160 times or more (converted in a standard state) relative to a unit catalyst volume per one hour.

(7) The production method as described in any one of (1) to (6) above.
wherein a concentration of the alkene contained in raw material gas to be supplied into the multitubular oxidation reactor is 7.5% by volume or less.

(8) The production method as described in any one of (1) to (7) above,
wherein the catalysts filled in all of the layers of the multitubular oxidation reactor are in a non-diluted state where dilution with an inert substance by physical mixing is not made.

(9) A method for producing acrolein and/or acrylic acid, or methacrolein and/or methacrylic acid, by the production method as described in any one of (1) to (8) above.

Effects of Invention

Even in a reaction under high-load circumstances, it is possible to produce, from an alkene, a corresponding unsaturated aldehyde and/or unsaturated carboxylic acid stably in a high yield while controlling the reaction bath temperature at a low level.

Mode for Carrying Out Invention

The present invention is concerned with a method for producing an unsaturated aldehyde and/or an unsaturated carboxylic acid, the method comprising subjecting an alkene to gas-phase catalytic partial oxidation with molecular oxygen by using a multitubular oxidation reactor having a complex metal oxide catalyst filled therein, thereby producing a corresponding unsaturated aldehyde and/or unsaturated carboxylic acid, wherein when preparing two or more kinds of catalysts having different formulations and stacking two or more layers in the axial direction of the tube, thereby achieving multilayer filling, the catalysts are filled in such a manner that not only the component amount of bismuth relative to molybdenum decreases from the gas inlet side toward the gas outlet side, but also the component amount of iron relative to molybdenum increases from the gas inlet side toward the gas outlet side.

The catalyst which is used in the present invention can be prepared through the following steps.

Step a): Preparation

In general, as for starting raw materials of respective elements constituting the catalyst, in the case of using an ammonium molybdate as a molybdenum component raw material, a high-performance catalyst is obtained. In particular, though the ammonium molybdate includes plural kinds of compounds, such as ammonium dimolybdate, ammonium tetramolybdate, ammonium heptamolybdate, etc. among those, the case of using ammonium heptamolybdate is the most preferred. In the case of using bismuth nitrate as a bismuth component raw material, a high-performance catalyst is obtained. As for raw materials of iron, cobalt, nickel, and other elements, oxides, or nitrates, carbonates, organic acid salts, hydroxides, and the like, each of which may become an oxide upon ignition, or mixtures thereof, can be generally used. For example, the iron component raw material and the cobalt component raw material and/or the nickel component raw material are dissolved in a desired ratio in water and mixed under a condition at 10 to 80° C.; the mixture is mixed with an aqueous solution or slurry of the separately prepared molybdenum component raw material and Z component raw material under a condition at 20 to 90° C.; after heating and stirring the resulting mixture for about 1 hour under a condition at 20 to 90° C., an aqueous solution having the bismuth component raw material dissolved therein and optionally the X component raw material and the Y component raw material are added, thereby obtaining an aqueous solution or slurry containing the catalyst components. The both are hereinafter collectively called "liquid preparation (A)". Here, the liquid preparation (A) is not always required to contain all of the catalyst constituent elements, and a part of those elements or a part of the amounts thereof may be added in the sequent step or steps. In addition, on the occasion of preparing the liquid preparation (A), when the amount of water for dissolving each of the component raw materials, or in the case of adding an acid, such as sulfuric acid, nitric acid, hydrochloric acid, tartaric acid, acetic acid, etc., for the purpose of dissolution, the acid concentration in the aqueous solution sufficient for dissolving the raw materials is not suitable for the preparation within the range of, for example, 5% by weight to 99% by weight, there may be the case where the form of the liquid preparation (A) becomes a clay-like lump. In this case, an excellent catalyst is not obtained. In particular, it is preferred that in dissolving the molybdenum component raw material, the molybdenum component raw material is constituted of only an ammonium molybdate, and the weight of water for dissolution is 8.5 times or less relative to the weight of molybdenum contained in the ammonium molybdate; and that in dissolving the bismuth component raw material, the bismuth component raw material is constituted of only bismuth nitrate, the weight of a nitric acid aqueous solution for dissolution is 2.3 times or more relative to the weight of bismuth contained in the bismuth nitrate, and the concentration of nitric acid of the nitric acid aqueous solution for dissolving bismuth nitrate is 10% by weight or more. The form of the thus-obtained liquid preparation (A) is preferably an aqueous solution or slurry from the standpoint that an excellent catalyst is obtained. Here, as for the constituent element ratios, ratios of bismuth that is one of the catalyst main components, and nickel and an alkali metal, each of which largely influences the activity, are important. The case where d/a that is a ratio of nickel to bismuth is 1.9 or more and 3.2 or less, d/g that is a ratio of nickel to the alkali metal is 29 or more and 69 or less, and a/g that is a ratio of bismuth to the alkali metal is 18 or more 35 or less is preferred because an excellent catalyst which is high in terms of yield of a target product and also high in terms of mechanical strength is provided.

Step b): Drying

Subsequently, the liquid preparation (A) obtained above is dried to form a dry powder. The drying method is not particularly limited so long as it is a method capable of completely drying the liquid preparation (A); however, examples thereof include drum drying, freeze drying, spray drying, evaporation to dryness, and the like. Of these, spray drying in which the slurry can be dried into a powder or granule within a short period of time is especially preferred in the present invention. Although the drying temperature of spray drying varies depending upon the concentration of slurry, the liquid sending speed, or the like, it is approximately 70 to 150° C. in terms of a temperature at the outlet of a drying machine. In addition, it is preferred to perform drying such that an average particle diameter of the dry powder obtained on that occasion is 10 to 700 μm. There is thus obtained a dry powder (B).

Step c): Preliminary Calcination

When the obtained dry powder (B) is calcined under air circulation at 200° C. to 600° C., and preferably 300° C. to 600° C., shaping properties, mechanical strength, and catalytic performance of the resulting catalyst tend to be improved. A calcination time is preferably 1 hour to 12 hours. There is thus obtained a preliminarily calcined powder (C).

Step d): Shaping

Although the shaping method is not particularly limited, on the occasion of shaping in a cylindrical or annular form, a method using a tablet shaping machine, an extrusion shaping machine, or the like is preferred. The case of shaping in a spherical form is more preferred, and the preliminarily calcined powder (C) may be shaped in a spherical form by using a shaping machine; however, a method of supporting the preliminarily calcined powder (C) (including a shaping auxiliary agent and a strength improver, if desired) on a carrier, such as an inert ceramic, etc., is preferred. Here, as for the supporting method, a tumbling granulation method, a method using a centrifugal flow coating apparatus, a wash coating method, and the like are widely known, and the supporting method is not particularly limited so long as it is a method capable of uniformly supporting the preliminarily calcined powder (C) on the carrier. However, in the case of taking into account the production efficiency of the catalyst or the performance of the prepared catalyst, more preferably, a method in which using an apparatus having a flat or uneven disk in a bottom of a fixed cylindrical vessel, a carrier charged within the vessel is vigorously agitated by means of rotation motion and revolution motion of the disk itself by rotating the disk at a high speed, and the preliminarily calcined powder (C) and optionally a shaping auxiliary agent and/or a strength improver or a pore-forming agent, are added thereto, thereby supporting the powder components on the carrier is preferred. It is to be noted that on the occasion of supporting, it is preferred to use a binder. Specific examples of the binder which may be used include water, ethanol, methanol, propanol, a polyhydric alcohol, polyvinyl alcohol that is a polymer-based binder, a silica sol aqueous solution that is an inorganic binder, and the like; ethanol, methanol, propanol, and a polyhydric alcohol are preferred; and a diol, such as ethylene glycol, etc., a triol, such as glycerin, etc., and the like are more preferred. By using an appropriate amount of a glycerin aqueous solution, the shaping properties become good, and a high-performance catalyst having high mechanical strength is obtained. Specifically, in the case of using an aqueous solution having a glycerin concentration of 5% by weight or more, a catalyst having an especially high performance is obtained. The use amount of such a binder is generally 2 to 80 parts by weight based on 100 parts by weight of the preliminarily calcined powder (C). As for the inert carrier, a carrier having a diameter of about 2 to 8 mm is generally used, and the preliminarily calcined powder (C) is supported thereon. Its supporting rate is determined taking into account a reaction condition, for example, a space velocity of the reaction raw materials, raw material concentrations, or the like, and it is generally 20% by weight to 80% by weight. Here, the supporting rate is expressed according to the following formula (3). There is thus obtained a shaped body (D).

Supporting rate (% by weight)=100×[(Weight of preliminarily calcined powder (C) used for shaping)/{(Weight of preliminarily calcined powder (C) used for shaping)+(Weight of inert carrier used for shaping)+(Weight of shaping auxiliary agent and strength improver used for shaping)}]    Formula (3)

Step e): Full-Scale Calcination

By calcining the shaped body (D) at a temperature of 200 to 600° C. for about 1 to 12 hours, its catalytic activity and effective yield tend to be improved. The calcination temperature is preferably 400° C. or higher and 600° C. or lower, and more preferably 500° C. or higher and 600° C. or lower. Air is simple and easy and preferred as the gas to be circulated; however, besides, it is also possible to use nitrogen or carbon dioxide as an inert gas, or a nitrogen oxide-containing gas, an ammonia-containing gas, a hydrogen gas, or a mixture thereof for the purpose of rendering the system into a reducing atmosphere. There is thus obtained a catalyst (E). When the calcination temperature is made high, the activity can be properly controlled. Such a catalyst can be used, for example, on the raw material gas inlet side on which a hot spot is generated.

The mechanical strength of the catalyst (E) is also largely influenced by the atomic ratios of the catalyst formulation. That is, the mechanical strength of the catalyst (E) is influenced by the kind of a compound to be formed by regulating the atomic ratios, or the matter that even in the same compound, the phase form of a crystal structure is different. In addition, the diameter of the complex metal oxide particle formed in the preparation step or drying step or the geometric structure of the particle, and the coagulation form thereof change, and therefore, the mechanical strength of the catalyst (E) is also influenced by changes in micro physical properties, such as strength of the compound crystal in the complex metal oxide, or macro physical properties, for example, the particle size distribution of the preliminarily calcined powder. Overall physical properties including not only the preparation method of each step but also the influence of the atomic ratios determine the mechanical strength of the ultimately prepared catalyst. An attrition resistance that is an index expressing the mechanical strength was calculated by using data measured by an attrition resistance tester, tablet, manufactured by Hayashi Rikagaku K. K. In the measurement, the catalyst was rotated 25 rpm for 10 minutes and then sieved by a standard sieve having a sieve opening of 1.70 mm, and the weight of the catalyst on the sieve was measured, thereby determining the attrition resistance according to the following formula (4). It may be said that the smaller the value of attrition resistance, the more excellent the mechanical strength is. The attrition resistance is preferably 3% by weight or less, more preferably 1.5% by weight or less, and still more preferably 0.5% by weight or less.

Attrition resistance (% by weight)=100×[{(Catalyst weight)−(Catalyst weight remaining on the sieve)}/(Catalyst weight)]    Formula (4)

The catalytic gas-phase oxidation reaction of an alkene using the complex oxide catalyst obtained by the present invention can be carried out by introducing a mixed gas composed of 1 to 10% by volume of an alkene, 5 to 18% by volume of molecular oxygen, 0 to 60% by volume of steam, and 20 to 70% by volume of an inert gas, for example, nitrogen, carbon dioxide, etc., in terms of a raw material gas formulation onto the catalyst prepared above at a temperature ranging from 250 to 450° C. under a pressure of atmospheric pressure to 10 atms under a supply load of the alkene of 60 to 200 $hr^{-1}$ in terms of a space velocity. In order that the present invention may be more effectively exhibited, the space velocity is preferably 100 to 200 hr$^{-1}$, and more preferably 120 to 200 hr$^{-1}$. On the occasion of practical use in the industrial plant, with respect to the space velocity at which the plant is usually operated, the operation is carried out while decreasing, the space velocity without exchanging the catalyst in order to achieve production adjustment due to deteriorating market conditions of a target product, or the like. At this time, a technique capable of coping with the space velocity over a wide range is demanded. This invention is excellent from the standpoint that not only it is able to cope with a high-load reaction, but also the effects of the invention are exhibited even under a relatively low load. In addition, in a high-load reaction, in the case where the raw material concentration is high, the heat generation caused due to the oxidation reaction tends to become large, and hence, the amount of the alkene is more preferably 7.5% by volume or less. Here, an alkene space velocity ($SV_0$) means the raw material load, and for example, the introduction at an alkene space velocity ($SV_0$) of 100 hr$^{-1}$ means that the gas-phase catalytic oxidation reaction is carried out while supplying the alkene in an amount of 100 times (converted in a standard state) relative to a unit catalyst volume per one hour. The alkene as referred to in the present invention also includes an alcohol capable of producing an alkene in its intramolecular dehydration reaction, for example, tertiary butanol.

EXAMPLES

Examples are hereunder described by reference to specific examples, but it should be construed that the present invention is not limited to these Examples so long as the gist of the present invention is not deviated.

Catalyst 1

2,000 parts by weight of ammonium heptamolybdate was completely dissolved in 7,600 parts by weight of pure water (in a weight of 7.0 times the weight of molybdenum) warmed at 60° C. Subsequently, 9.2 parts by weight of potassium nitrate was dissolved in 104.1 parts by weight of pure water and added to the above-described solution. Subsequently, 686.4 parts by weight of ferric nitrate, 1,428.8 parts by weight of cobalt nitrate, and 768.6 parts by weight of nickel nitrate were dissolved in 1,528.4 parts by weight of pure water warmed at 60° C. These solutions were gradually mixed while stirring. Thereafter, a solution prepared by adding 778.4 parts by weight of bismuth nitrate to a nitric acid aqueous solution (in a weight of 3.1 times the weight of bismuth in bismuth nitrate to be dissolved) which had been prepared by adding 198.2 parts by weight of nitric acid (60% by weight) to 825.2 parts by weight of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 6 hours. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 560° C., thereby obtaining Spherical Catalyst 1 having an average particle diameter of 5.2 mm according to the present invention. The catalyst calculated from the charged raw materials was found to be a complex metal oxide having the following atomic ratios.

$d/a=1.6, d/g=29, a/g=18$

Mo:Bi:Fe:Co:Ni:K=12:1.7:1.8:5.2:2.8:0.096

Catalyst 2

2,000 parts by weight of ammonium heptamolybdate was completely dissolved in 7,600 parts by weight of pure water (in a weight of 7.0 times the weight of molybdenum) warmed at 60° C. Subsequently, 4.4 parts by weight of potassium nitrate was dissolved in 50.1 parts by weight of pure water and added to the above-described solution. Subsequently, 953.3 parts by weight of ferric nitrate, 1,786.0 parts by weight of cobalt nitrate, and 713.7 parts by weight of nickel nitrate were dissolved in 1,830.1 parts by weight of pure water warmed at 60° C. These solutions were gradually mixed while stirring. Thereafter, a solution prepared by adding 503.7 parts by weight of bismuth nitrate to a nitric acid aqueous solution (in a weight of 3.1 times the weight of bismuth in bismuth nitrate to be dissolved) which had been prepared by adding 128.3 parts by weight of nitric acid (60% by weight) to 534.0 parts by weight of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 6 hours. Crystalline cellulose was added in proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 2 having an average particle diameter of 5.2 mm according to the present invention. The catalyst calculated from the charged raw materials was found to be a complex metal oxide having the following atomic ratios.

$d/a=2.4, d/g=56, a/g=24$

Mo:Bi:Fe:Co:Ni:K=12:1.1:2.5:6.5:2.6:0.0461

Catalyst 3

2,000 parts by weight of ammonium heptamolybdate was completely dissolved in 7,600 parts by weight of pure water (in a weight of 7.0 times the weight of molybdenum) warmed at 60° C. Subsequently, 4.4 parts by weight of potassium nitrate was dissolved in 50.1 parts by weight of pure water and added to the above-described solution. Subsequently, 762.7 parts by weight of ferric nitrate, 1,786.0 parts by weight of cobalt nitrate, and 823.5 parts by weight of nickel nitrate were dissolved in 1,787.3 parts by weight of pure water warmed at 60° C. These solutions were gradually mixed while stirring. Thereafter, a solution prepared by adding 457.9 parts by weight of bismuth nitrate to a nitric acid aqueous solution (in a weight of 3.1 times the weight of bismuth in bismuth nitrate to be dissolved) which had been prepared by adding 116.6 parts by weight of nitric acid (60% by weight) to 485.5 parts by weight of pure water, thereby regulating a nitric acid concentration to 12% by weight and then completely dissolving was added to the foregoing solution and mixed with stirring. This slurry was dried by a spray drying method, and the resulting dry powder was preliminarily calcined at a maximum temperature 440° C. for 6 hours. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 520° C., thereby obtaining Spherical Catalyst 3 having an average particle diameter of 5.2 mm according to the present invention. The catalyst calculated from the charged raw materials was found to be a complex metal oxide having the following atomic ratios.

$d/a=3.0, d/g=65, a/g=22$

Mo:Bi:Fe:Co:Ni:K=12:1.0:2.0:6.5:3.0:0.046

Catalyst 4

2,000 parts by weight of ammonium heptamolybdate was completely dissolved in 7,600 parts by weight of pure water (in a weight of 7.0 times the weight of molybdenum) warmed at 60° C. Subsequently, 9.2 parts by weight of potassium nitrate was dissolved in 104.1 parts by weight of pure water and added to the above-described solution. Subsequently, 877.1 parts by weight of ferric nitrate, 1,373.9 parts by weight of cobalt nitrate, and 768.6 parts by weight of nickel nitrate were dissolved in 1,600.4 parts by weight of pure water warmed at 60° C. These solutions were gradually mixed while stirring. Thereafter, a solution prepared by adding 595.3 parts by weight of bismuth nitrate to a nitric acid aqueous solution (in a weight of 3.0 times the weight of bismuth in bismuth nitrate to be dissolved) which had been prepared by adding 151.6 parts by weight of nitric acid (60% by weight) to 631.1 parts by weight of pure water, thereby regulating a nitric acid concentration to 12% by weight and then completely dissolving was added to the foregoing solution and mixed with stirring. This slurry was dried by a spray drying method and the resulting dry powder was preliminarily calcined at a maximum temperature 440° C. for 6 hours. Crystalline cellulose was added in a proportion of 5% by weight relative to the preliminarily calcined powder and thoroughly mixed. Thereafter, the mixture was supported and shaped in a spherical form in a supporting amount of 50% by weight on an inert spherical carrier by using a 30% by weight glycerin solution as a binder by a tumbling granulation method. Subsequently, calcination was carried out such that the temperature after 12 hours was 530° C., thereby obtaining Spherical Catalyst 4 having an average particle diameter of 5.2 mm according to the present invention. The catalyst calculated front the charged raw materials was found to be a complex metal oxide having the following atomic ratios.

$d/a=2.2, d/g=29, a/g=13$

Mo:Bi:Fe:Co:Ni:K=12:1.3:2.3:5.0:2.8:0.0964

Catalyst 5

Catalyst 5 for comparison was obtained in the same manner as in Catalyst 1, except that only the calcination step temperature after shaping was changed to 530° C.

Catalyst 6

Catalyst 6 for comparison was obtained in the same manner as in Catalyst 1, except that only the calcination step temperature after shaping was changed to 520° C.

Catalyst 7

Catalyst 7 according to the present invention was obtained in the same as in Catalyst 1, except that the diameter of the inert spherical carrier to be used for shaping was set to 4.0 mm; and that the average particle diameter of the shaped body was set to 4.7 mm.

Catalyst 8

Catalyst 8 according to the present invention was obtained in the same as in Catalyst 3, except that the diameter of the inert spherical carrier to be used for shaping was set to 4.0 mm; that the average particle diameter of the shaped body was set to 4.7 mm; and that the calcination step temperature after shaping was changed to 530° C.

Catalyst 9

Catalyst 9 for comparison was obtained in the same manner as in Catalyst 4, except that only the calcination step temperature after shaping was changed to 520° C.

Example 1

A gas-phase catalytic oxidation reaction of propylene was carried out by using Catalysts 1 and 2, thereby determining catalytic performances represented by a propylene conversion, an acrolein yield, an acrylic acid yield, and an effective yield. Catalyst 1 was filled in a filling length of 1,500 mm on the raw material gas inlet side of a stainless steel-made reaction tube having a diameter of 25.4 mm, in which a thermocouple protection tube having an outer diameter of 3.2 mm was placed; and Catalyst 2 was filled in a filling length of 2,000 mm on the raw material gas outlet side. A mixed gas composed of 7.4% by volume of propylene, 63.2% by volume of air, 7.4% by volume of steam, and 22.1% by volume of nitrogen as a raw material gas was introduced at a propylene space velocity ($SV_0$) of 165 $hr^{-1}$ from the reaction tube inlet, a pressure on the gas outlet side was adjusted at 110 kPaG, and the gas-phase catalytic partial oxidation reaction of propylene was carried out. The results when the effective yield at the moment at which the reaction elapsed about 300 hours became maximum are shown in Table 1.

Example 2

The gas-phase catalytic oxidation reaction of propylene was carried out in the same manner as in Example 1, except that Catalyst 3 was filled on the raw material gas outlet side in place of the Catalyst 2. The results when the effective yield at the moment at which the reaction elapsed about 300 hours became maximum are shown in Table 1.

Comparative Example 1

The oxidation reaction of propylene was carried out in the same manner as in Example 1, except that the filling was changed to diluted three-layer filling with Catalyst 4. The diluted three-layer filling was carried out in such a manner that the catalyst concentration became high in the order of the upper layer to the intermediate layer to the lower layer, from the gas inlet side toward the gas outlet side. As for the upper layer, the catalyst was diluted with an inert substance composed mainly of silica and alumina and having an average particle diameter of 5.2 mm such that the catalyst weight was 70% by weight, and then filled in a filling length of 700 mm. Subsequently, as for the intermediate layer, the catalyst was diluted with the above-described inert substance such that the catalyst weight was 85% by weight, and then filled in a filling length of 500 mm. Finally, as for the lower layer, the catalyst was filled such that the catalyst weight was 100% by weight; and that the filling length was 2,300 mm. The results when the effective yield at the moment at which the reaction elapsed about 300 hours became maximum are shown in Table 1. It is to be noted that in the case where Catalyst 4 was filled without being diluted and allowed to react, the hot spot temperature became excessively high, so that it was difficult to keep the stable reaction state.

Example 3

The gas-phase catalytic oxidation reaction was carried out in the same manner as in Example 2, except that the propylene space velocity ($SV_0$) was changed to 120 $hr^{-1}$; and that the pressure on the gas outlet side was changed to 70 kPaG. The results when the effective yield at the moment at which the reaction elapsed about 300 hours became maximum are shown in Table 1.

Comparative Example 2

The oxidation reaction of propylene was carried out in the same manner as in Example 3, except that the filling was changed to diluted two-layer filling with Catalyst 5 and Catalyst 6. The diluted two-layer filling was carried out in such a manner that the catalyst concentration became high in the order of the upper layer to the lower layer, from the gas inlet side toward the gas outlet side. As for the upper layer, Catalyst 5 was diluted with an inert substance composed mainly of silica and alumina and having an average particle diameter of 5.2 mm such that the catalyst weight was 70% by weight, and then filled in a filling length of 1,500 mm. As for the lower layer, Catalyst 6 was filled such that the catalyst weight was 100% by weight; and that the filling length was 2,000 mm. The results when the effective yield at the moment at which the reaction elapsed about 300 hours became maximum are shown in Table 1. It is to be noted that in the case where Catalyst 5 was filled without being diluted and allowed to react, the hot spot temperature became excessively high, so that it was difficult to keep the stable reaction state.

Example 4 gas-phase catalytic oxidation reaction of propylene was carried out by using Catalysts 7 and 8, thereby determining a propylene conversion, an acrolein yield, an acrylic acid yield, and an effective yield. Catalyst 7 was filled in a filling length of 1,500 mm on the raw material gas inlet side of a stainless steel-made reaction tube having a diameter of 25.4 mm, in which a thermocouple was placed; and Catalyst 8 was filled in a filling length of 3,000 mm on the raw material gas outlet side. A mixed gas composed of 7.2% by volume of propylene, 65.3% by volume of air, and 27.4% by volume of steam as a raw material gas was introduced at a propylene space velocity ($SV_0$) of 140 $hr^{-1}$ from the reaction tube inlet, a pressure on the gas outlet side was adjusted at 90 kPaG, and the gas-phase catalytic partial oxidation reaction of propylene was carried out. The results when the effective yield at the moment at which the reaction elapsed about 300 hours became maximum are shown in Table 1.

Comparative Example 3

The oxidation reaction of propylene was carried out in the same manner as in Example 4, except that the filling was changed to diluted two-layer filling with Catalyst 9. The diluted two-layer filling was carried out in such a manner that the catalyst concentration became high in the order of the upper layer to the lower layer, from the gas inlet side toward the gas outlet side. As for the upper layer, Catalyst 9 was diluted with an inert substance composed mainly of silica and alumina and having an average particle diameter of 5.2 mm such that the catalyst weight was 70% by weight, and then filled in a filling length of 1,500 mm. As for the lower layer. Catalyst 9 was filled such that the catalyst weight was 100% by weight; and that the filling length was 3,000 mm. The results when the effective yield at the moment at which the reaction elapsed about 300 hours became maximum are shown in Table 1. It is to be noted that in the case where Catalyst 9 was filled without being diluted and allowed to react, the hot spot temperature became excessively high, so that it was difficult to keep the stable reaction state.

TABLE 1

| | Catalyst | Reaction bath temperature (° C.) | Maximum reaction temperature (° C.) | Propylene conversion (mol %) | Acrolein yield (A) (mol %) | Acrylic acid yield (B) (mol %) | Effective yield (A + B) (mol %) |
|---|---|---|---|---|---|---|---|
| Example 1 | Catalyst 1 & Catalyst 2 | 335 | 422 | 98.4 | 82.4 | 8.8 | 91.2 |
| Example 2 | Catalyst 1 and Catalyst 3 | 337 | 423 | 98.6 | 82.2 | 8.9 | 91.1 |
| Comparative Example 1 | Catalyst 4 | 346 | 430 | 97.8 | 81.8 | 8.2 | 90.0 |
| Example 3 | Catalyst 1 & Catalyst 3 | 333 | 406 | 98.4 | 84.0 | 7.9 | 91.9 |
| Comparative Example 2 | Catalyst 5 & Catalyst 6 | 337 | 442 | 98.4 | 82.2 | 8.4 | 90.6 |
| Example 4 | Catalyst 7 & Catalyst 8 | 330 | 426 | 98.0 | 81.9 | 7.5 | 89.4 |
| Comparative Example 3 | Catalyst 9 | 335 | 425 | 97.0 | 80.2 | 8.4 | 88.6 |

In the light of the above, by using the technique of the present invention, even in a high-load reaction, not only the maximum reaction temperature can be kept at the same degree or controlled at a low level, but also the reaction bath temperature can be controlled at a low level, and hence, a target product can be obtained stably in a high yield.

While the invention has been described in detail and with reference to specific embodiments thereof, it will be apparent to one skilled in the art that various changes and modifications can be made therein without departing from the spirit and scope thereof.

It is to be noted that the present application is based on a Japanese patent application filed on Jul. 18, 2013 (Japanese Patent Application No. 2013-149136), the entireties of which are incorporated by reference. In addition, all references cited herein are incorporated as a whole.

INDUSTRIAL APPLICABILITY

The present invention is useful for the industrial plant of producing an unsaturated aldehyde or an unsaturated carboxylic acid.

The invention claimed is:

1. A method for producing an unsaturated aldehyde and/or an unsaturated carboxylic acid, the method comprising:
subjecting an alkene to gas-phase catalytic partial oxidation with molecular oxygen by using a multitubular oxidation reactor having a complex metal oxide catalyst filled therein, thereby producing a corresponding unsaturated aldehyde and/or unsaturated carboxylic acid,
wherein when preparing two or more kinds of catalysts having different formulations and stacking two or more layers in an axial direction of a tube, thereby achieving multilayer filling, the catalysts are filled in such a manner that not only a component amount of bismuth relative to molybdenum decreases from a gas inlet side toward a gas outlet side, but also a component amount of iron relative to molybdenum increases from the gas inlet side toward the gas outlet side.

2. The production method according to claim 1,
wherein the catalyst for producing an unsaturated aldehyde and/or an unsaturated carboxylic acid contains a compound represented by the following formula (1), the catalyst being prepared by a method in which in a step of preparing the compound represented by the following formula (1): a molybdenum component raw material is constituted of only an ammonium molybdate, and a weight of water for dissolution is 8.5 times or less relative to a weight of molybdenum contained in the ammonium molybdate; a bismuth component raw material is constituted of only bismuth nitrate, a weight of a nitric acid aqueous solution for dissolution is 2.3 times or more relative to a weight of bismuth contained in the bismuth nitrate, and a concentration of nitric acid of the nitric acid aqueous solution for dissolving bismuth nitrate therein is 10% by weight or more, and is filled in at least one layer on the most gas outlet side in the tube axis:

$$Mo_{12}Bi_aFe_bCO_cNi_dX_eY_fZ_gO_h \quad \text{Formula (1)}$$

wherein X is at least one element selected from the group consisting of magnesium (Mg), calcium (Ca), manganese (Mn), copper (Cu), zinc (Zn), cerium (Ce) and samarium (Sm); Y is at least one element selected from the group consisting of boron (B), phosphorus (P), arsenic (As), antimony (Sb) and tungsten (W); Z is at least one element selected from the group consisting of sodium (Na), potassium (K), rubidium (Rb) and cesium (Cs); a to g represent atomic ratios of the respective components; h is a numerical value determined by degrees of oxidations of the catalyst components; a=0.80 to 2.0; b=1 to 2.5; c=3 to 7; d=2 to 3.5; e=0 to 10; f=0 to 10; g=0.01 to 0.10; h is expressed by the numerical value satisfying the oxidation states of other elements; d/a is 1.9 or more and 3.2 or less; d/g is 29 or more and 69 or less; and a/g is 18 or more and 35 or less.

3. The production method according to claim 1,
wherein a form of the complex metal oxide catalyst is a spherical coating catalyst in which catalytic active components are supported on a surface of an inert carrier.

4. The production method according to claim 1,
wherein a load of the alkene in raw material gas to be supplied into the multitubular oxidation reactor is 120 times or more (converted in a standard state) relative to a unit catalyst volume per one hour.

5. The production method according to claim 1,
wherein a load of the alkene in raw material gas to be supplied into the multitubular oxidation reactor is 140 times or more (converted in a standard state) relative to a unit catalyst volume per one hour.

6. The production method according to claim 1,
wherein a load of the alkene in raw material gas to be supplied into the multitubular oxidation reactor is 160 times or more (converted in a standard state) relative to a unit catalyst volume per one hour.

7. The production method according to claim 1,
wherein a concentration of the alkene contained in raw material gas to be supplied into the multitubular oxidation reactor is 7.5% by volume or less.

8. The production method according to claim 1,
wherein the catalysts filled in all of the layers of the multitubular oxidation reactor are in a non-diluted state where dilution with an inert substance by physical mixing is not made.

9. A method for producing acrolein and/or acrylic acid, or methacrolein and/or methacrylic acid, by the production method according to claim 1.

* * * * *